(12) United States Patent
Otten

(10) Patent No.: US 7,785,335 B2
(45) Date of Patent: Aug. 31, 2010

(54) DEVICE FOR CLAMPING ORGANIC TISSUE

(76) Inventor: Gert Otten, Bismarckstrasse 13, D-27619 Schiffdorf (DE)

(*) Notice: Subject to any disclaimer, the term of this patent is extended or adjusted under 35 U.S.C. 154(b) by 177 days.

(21) Appl. No.: 12/228,181

(22) Filed: Aug. 11, 2008

(65) Prior Publication Data

US 2009/0054917 A1    Feb. 26, 2009

Related U.S. Application Data

(63) Continuation of application No. 11/170,781, filed on Jun. 29, 2005, now abandoned.

(30) Foreign Application Priority Data

Jun. 29, 2004    (DE) .................... 10 2004 032 450

(51) Int. Cl.
     *A61B 17/08*    (2006.01)
(52) U.S. Cl. ..................................... 606/157
(58) Field of Classification Search .............. 623/23.72, 623/1.16, 1.36, 1.41, 1.42; 81/127, 128, 81/129, 129.5, 176.2; 606/139, 142, 151, 606/154, 157, 158; 24/522
     See application file for complete search history.

(56) References Cited

U.S. PATENT DOCUMENTS 4,651,737 A * 3/1987 Deniega .................. 606/158
5,340,360 A   8/1994 Stefanchik
7,291,161 B2 11/2007 Hooven
2004/0143267 A1 7/2004 Sturtz et al.
2004/0143276 A1 7/2004 Sturtz et al.

FOREIGN PATENT DOCUMENTS

| DE | 690 31 165 | 8/1998 |
| DE | 690 32 165 | 8/1998 |
| EP | 0 178 469  | 4/1986 |
| EP | 0 504 312  | 9/1992 |

* cited by examiner

*Primary Examiner*—Darwin P Erezo
*Assistant Examiner*—Christina Lauer
(74) *Attorney, Agent, or Firm*—Collard & Roe, P.C.

(57) ABSTRACT

A device for clamping off organic tissue has a tissue clamp with clamping bars in holders. A proximal clamping bar can be displaced in a guide groove of an application crosspiece by a tappet, while the distal clamping bar maintains its position until the tissue has been clamped off. The clamping bars have guide pin, or the distal clamping bar has a fixation shoulder. The pins or shoulder fit into crosswise grooves in the application crosspiece, and thus the clamping bars can be inserted into them vertically. The proximal clamping bar has a holder pin on its base that engages into a holder bore of the distal clamping bar. This produces a force-fit and shape-fit connection with this bore, while simultaneously clamping off the organic tissue. The guide pins shear off if the force required to clamp off the organic tissue is exceeded.

9 Claims, 2 Drawing Sheets

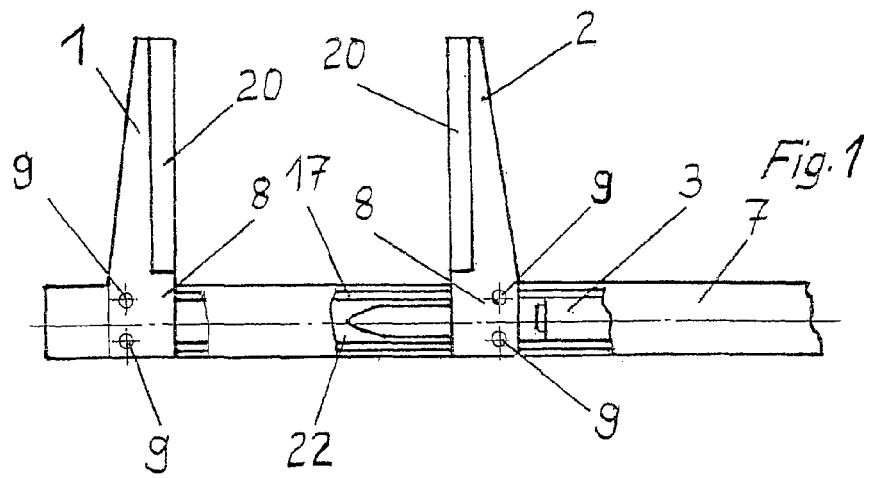
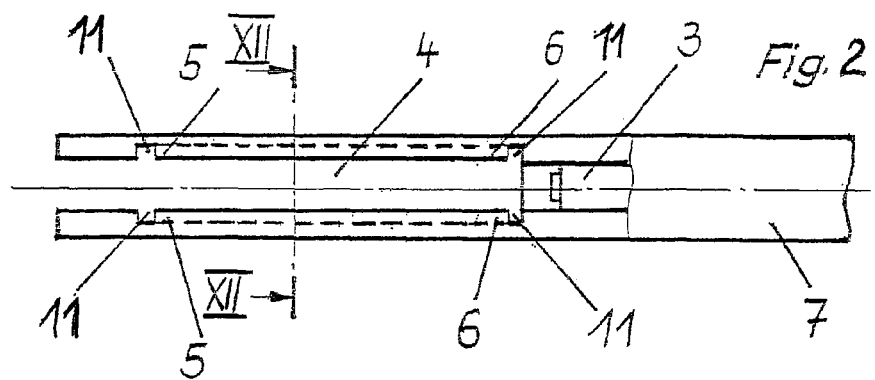
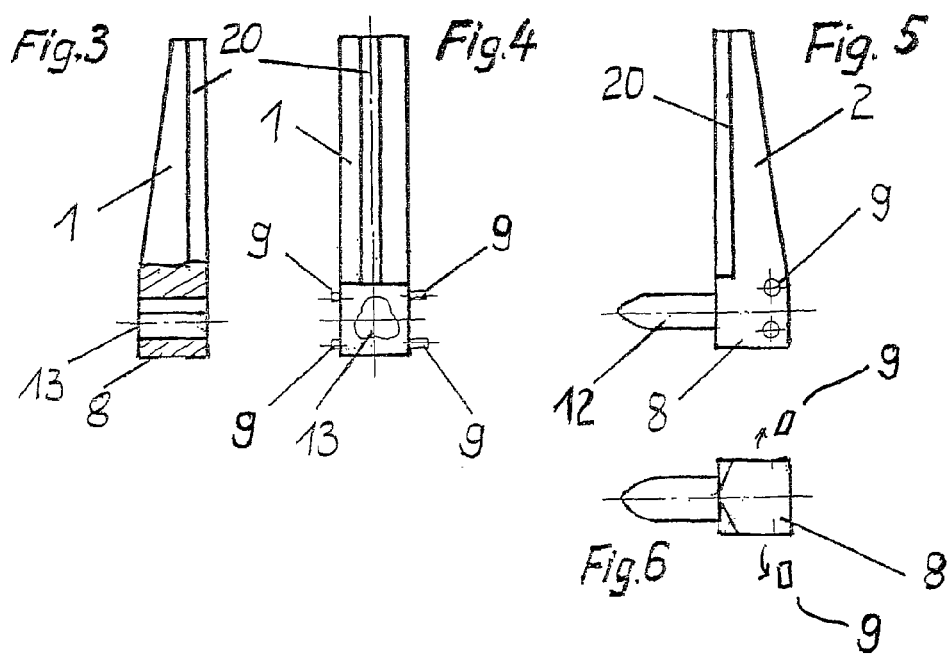

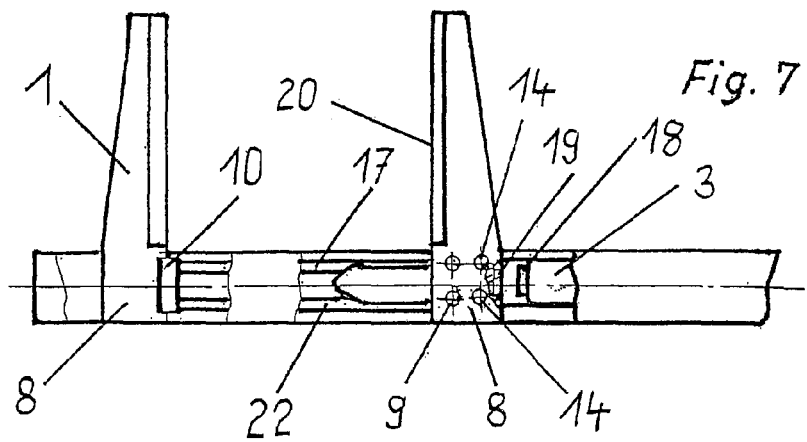
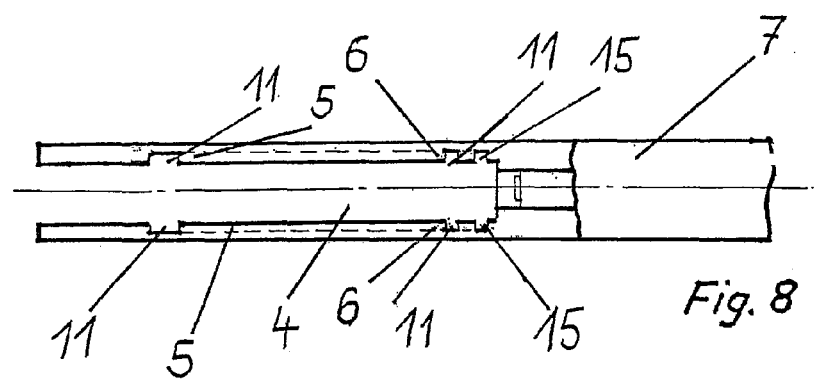
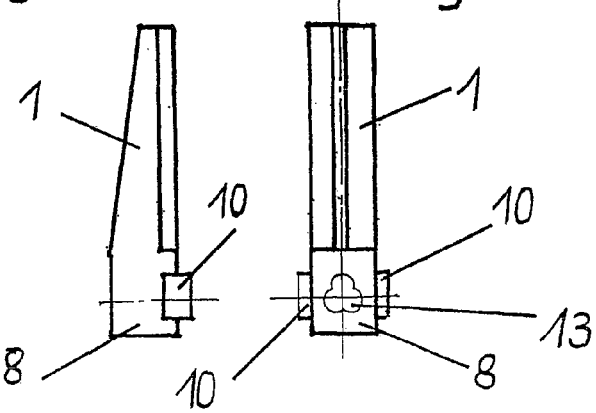
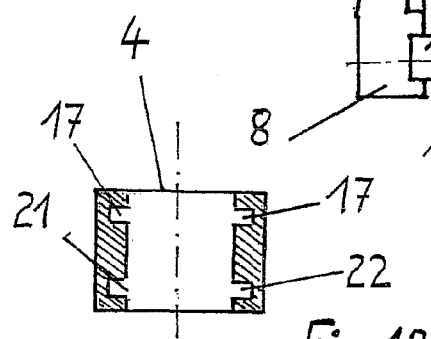
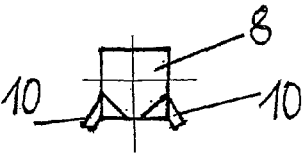

DEVICE FOR CLAMPING ORGANIC TISSUE

CROSS-REFERENCE TO RELATED APPLICATIONS

This application is a continuation under 35 U.S.C. §120 of U.S. patent application Ser. No. 11/170,781, filed on Jun. 29, 2005 now abandoned, which claims priority under 35 U.S.C. §119 of German Patent Application No. 10 2004 032 450.6, filed on Jun. 29, 2004.

BACKGROUND OF THE INVENTION

1. Field of the Invention

The invention relates to a device for clamping off organic tissue, particularly blood vessels. It can particularly be used in minimally invasive surgery.

2. The Prior Art

A device for clamping off organic tissue is described in European Patent No. EP 0 178 469. This device has a distal and a proximal clamping bar, which extend perpendicularly from an application crosspiece. The proximal clamping bar can be displaced in the direction of the distal clamping bar, and the tissue can be clamped off between them. Finally, the tissue clamp formed in this way can be removed from the application crosspiece by way of a tappet that surrounds the application crosspiece and is displaceable longitudinally to it, for which purpose a planned breaking point is assigned to the application crosspiece, and a locking and unlocking device is assigned to the base of the distal clamping bar. The disadvantages of this device can be seen as being, in particular, its complicated structure and its difficult handling.

In particular, it is difficult to equip the application crosspiece with the clamping bar. This presupposes that the proximal clamping bar is always disposed in front of the distal one. Furthermore, secure fixation of the clamping bars relative to one another, in their end position, is nearly impossible.

U.S. Pat. No. 4,651,737 describes a releasable device for clamping off organic tissue, in which the distal clamping bar can be connected with the application crosspiece by a journal-like connection. The proximal clamping bar, which can be displaced in the longitudinal direction with an internal pushing device, is disposed on the crosspiece. With this device, the clamping bars are pushed over one another, seizing the organic tissue, to such an extent that the tissue is finally fixed in place by a shearing/clamping effect, and the tissue clamp can subsequently be released from the application crosspiece, under a pressure that is not slight.

However, this device has the problem that the clamping bars, with their clamping crosspieces, which are partly meshed with gears, have a predetermined and unchangeable distance relative to one another during closing. As a result, step-free clamping of organic tissue, depending on the compression pressure, is not possible with this device. Clamping takes place without any consideration of the type of tissue and the existing conditions, such as the thickness of a blood vessel, for example. Because of the shearing/clamping effect by means of which the tissue is fixed in place, there is the risk of injury to the tissue, all the way to unintentionally cutting through tissue.

SUMMARY OF THE INVENTION

It is therefore an object of the invention to create a device of the type mentioned initially, which allows secure seizure and injury-free clamping of organic tissue, and the formation of a stable tissue clamp, with little effort. It is another object of the invention to provide a device that can be equipped with clamping bars in a simple manner, and furthermore can also be produced in cost-advantageous manner.

This task is accomplished, according to the invention, by a device for clamping off organic tissue, particularly blood vessels, having a tissue clamp that can be released from the distal end of an application instrument. The clamp has clamping bars made of absorbable material, each disposed in holders. A proximal clamping bar can be displaced in a guide groove of an application crosspiece by an internal pushing device, while the clamping bar disposed at the distal end maintains its position until the organic tissue has been clamped off. The application crosspiece is configured in one piece and the clamping bars have at least one guide pin at their base, on both sides, or the distal clamping bar has a fixation shoulder. The pins or shoulder are configured to fit into crosswise grooves provided in the application crosspiece, and thus the clamping bars can be inserted into them vertically to the axis of the application crosspiece. The proximal clamping bar can be displaced in the longitudinal direction, in the guide groove of the application crosspiece, and in longitudinal grooves formed on both sides. The grooves are provided on both insides of the application crosspiece, with the guide pins. The proximal clamping bar disposed on the application crosspiece has a holder pin on its base, disposed in the direction of the distal end of the application crosspiece. This pin engages into a corresponding holder bore of the clamping bar disposed distally when the proximal clamping bar is displaced by the tappet. This produces a force-fit and shape-fit connection with this bore, while simultaneously clamping off the organic tissue. The guide pins are dimensioned in such a manner that they shear off if the expenditure of force required to clamp off the organic tissue is exceeded.

Alternatively, the fixation shoulder has such an elasticity that the clamping bars, with the organic tissue clamped off between them, as a tissue clamp, can be released from the application crosspiece by the tappet, in the direction of the distal end.

In an advantageous embodiment of the device according to the invention, the proximal clamping bar has two guide pins, disposed in pairs in the longitudinal direction, on both sides, and the application crosspiece, corresponding to this, has two crosswise grooves on both sides, into which the guide pins engage when the proximal clamping bar is inserted into the application crosspiece.

It is furthermore advantageous if the face surface of the tappet and the opposite face surface of the base of the proximal clamping bar have corresponding profilings.

It has proven to be particularly advantageous if the holder pin and the holder bore, corresponding to one another, are configured to be slightly conical and/or cylindrical, cone-shaped or pyramid-shaped.

According to another embodiment of the invention, the holder pin and the holder bore have a corresponding cross-section to ensure that the clamping bars remain parallel while the organic tissue is clamped off, and to ensure secure reciprocal fixation of the clamping bars in the tissue clamp as an end position.

It is also advantageous if the clamping bars run slightly conically or biased relative to one another, so that they have a greater reciprocal distance close to the application crosspiece than at their end.

Furthermore, it is particularly advantageous if multiple longitudinal grooves are provided, and for this purpose, the cross-section of the guide groove on the inside of the application crosspiece is configured in T shape or double T shape, in which grooves the guide pins provided correspondingly on the base of the proximal clamping bar can be displaced.

In another embodiment, the fixation shoulder extends lengthwise in a crosswise groove, and is elastically configured in such a manner that when the force expenditure required for clamping off the organic tissue is exceeded, it deforms so that the tissue clamp can be displaced and released out of the application crosspiece by means of the tappet.

The invention has the advantage that the organic tissue can be clamped off without injury, by means of a simple pressing/clamping mechanism that is dependent on the compression pressure, in a step-free manner. The distance between the clamping bars in the end state is limited only by the tissue resistance. Unintentionally cutting the tissue through is thereby precluded.

The device according to the invention can be handled easily. Since the two clamping bars can be disposed on the application crosspiece in simple manner, after organic tissue has been clamped off and the tissue clamp has been released, the application crosspiece can be equipped with new clamping bars again, in a fast and uncomplicated manner, and thus prepared for further use.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views:

FIG. 1 shows a front view of a device according to the invention, in a partially sectional representation;

FIG. 2 shows a top view of the device according to FIG. 1;

FIG. 3 shows a front view of the distal clamping bar according to FIG. 1, partly in section;

FIG. 4 shows a side view of the distal clamping bar according to FIG. 3;

FIG. 5 shows a front view of the proximal clamping bar according to FIG. 1;

FIG. 6 shows a top view of the proximal clamping bar according to FIG. 5;

FIG. 7 shows a front view of a special embodiment of the device according to the invention, partly in section;

FIG. 8 shows a top view of the application crosspiece of the device according to FIG. 7;

FIG. 9 shows a front view of the distal clamping bar according to FIG. 7, with fixation shoulder;

FIG. 10 shows a side view of the distal clamping bar according to FIG. 9;

FIG. 11 shows a top view of the clamping bar according to FIG. 10; and

FIG. 12 shows the section XII-XII according to FIG. 2.

DETAILED DESCRIPTION OF THE PREFERRED EMBODIMENT

As is evident from FIG. 1, the device for clamping off organic tissue, particularly blood vessels, has an application crosspiece 7 that extends in the distal direction from a proximal base body not described in greater detail here. With the base body, application crosspiece 7 is connected with an application instrument, also not shown. Within application crosspiece 7, a tappet 3 can be displaced as an internal pushing device, essentially over the entire length of a guide groove 4, in the longitudinal direction, by means of this instrument. Clamping bars 1 and 2 are disposed on application crosspiece 7; the organic tissue can be clamped off between their clamping crosspieces 20. Clamping bars 1 and 2 extend from their base 8 perpendicular to application crosspiece 7, and are disposed parallel to one another. However, it is also possible that clamping bars 1 and 2 run slightly conically toward one another with their clamping crosspieces 20, or are biased, so that when clamping bars 1 and 2 are brought together, their ends that are at a distance from the application crosspiece come to rest against one another first. This has the advantage that organic tissue can be seized more easily and securely held between the clamping bars as they are brought towards one another.

In order to avoid injury to the organic tissue to be clamped off, particularly blood vessels, the clamping crosspieces 20 are configured to be blunt at their ends that lie opposite one another, as can be seen in FIGS. 4, 6, 10, and 11.

Bases 8 of clamping bars 1 and 2 each have guide pins 9, which are configured to fit into crosswise grooves 11 provided on both sides of the application crosspiece 7 (FIG. 2). Clamping bars 1 and 2 can be pushed into these crosswise grooves 11 with their guide pins 9, from above, perpendicular to application crosspiece 7, onto the holders 5, 6. When proximal clamping bar 2 is displaced, guide pins 9 or 9 and 14, respectively, make a transition into longitudinal grooves 17 or 17, 21, and 22, respectively, provided on the insides of application crosspiece 7. According to FIG. 12, the cross-section of guide groove 4 on the inside of application crosspiece 7 is configured in T shape or double T shape, and thus forms additional longitudinal grooves 21; 22, into which guide pins 9, 14 correspondingly formed on base 8 of proximal clamping bar 2 can now be displaced.

In order to increase the precision of the guidance of proximal clamping bar 2, two guide pins 9, 14 disposed in pairs on both sides, in each instance, in the longitudinal direction, relative to one another, are provided on its base 8 according to FIG. 7. Application crosspiece 7, corresponding to them, in each instance, possesses two crosswise grooves 11, 15, on both sides, into which guide pins 9, 14 can be introduced when proximal clamping bar 2 is introduced into application crosspiece 7.

Proximal clamping bar 2 can be displaced by tappet 3, in the direction of distal clamping bar 1. From FIG. 7, it is evident that for this purpose, it is practical if face surface 18 of tappet 3 engages into a correspondingly shaped face surface 19 on the back of holder pin 12. In this way, the positioning of the proximal clamping bar 2 can be significantly supported.

From FIGS. 1, 5, 6, and 7, proximal clamping bar 2 has a holder pin 12 disposed in the direction of the distal end, which pin engages into holder bore 13 configured coaxially in clamping bar 1 when proximal clamping bar 2 is displaced (FIG. 3, 4, 10). Holder pin 12 and holder bore 13 are assigned to bases 8 of clamping bars 1, 2, so that they lie outside of the actual clamping region. Holder pin 12 and holder bore 13 have a corresponding cross-section and a corresponding shape, in each instance, which permit force-fit and shape-fit interaction when clamping off the organic tissue. As shown in FIG. 10, in the present example, the cross-section is formed by three overlapping circles. However, any other geometric shape of the cross-section is also possible, if it is guaranteed that clamping bars 1, 2 are brought together with a shape fit. In terms of their shape, holder pin 12 and holder bore 13 can be configured correspondingly, for example in pyramid shape or cone shape, or cylindrically.

By means of the corresponding shaping and the corresponding cross-section, the tissue can be clamped off without injury, by a simple pressing/clamping mechanism, as clamping bars 1, 2 are brought together in a step-free manner. For this purpose, the proximal clamping bar 2 is pushed in the direction of distal clamping bar 1, by means of tappet 3, until the two of them are permanently connected to form a tissue clamp, in their end position, and the tissue positioned between them has been clamped off. For this purpose, holder pin 12 has entered into holder bore 13, forming a force-fit and shape-fit connection. Finally, the tissue clamp is pushed down off application crosspiece 7 with tappet 3, and separate from it. Guide pins 9, 14 are dimensioned in such a manner that they shear off in the case of increased pressure of the tappet 3 on the distal side of holder 5, 6, or respectively, fixation shoulder 10 exits from the crosswise groove 11, and allows the tissue clamp to be pushed out because of its elasticity. Shearing off of guide pins 9, 14 takes place because longitudinal grooves 17, 21, 22 open into the distal holders, and are not continued all the way to the distal face side of application crosspiece 7.

As is furthermore evident from FIG. 7, base 8 of distal clamping bar 1 can have an elastic fixation shoulder 10 that engages into the corresponding crosswise groove 11 over its entire length (FIG. 8, 9, 10, 11). The fixation shoulder is elastic and dimensioned in such a manner that it fixes the distal clamping bar 1 securely in holder 5, but releases clamping bar 1 again as soon as the pressure of tappet 3 exceeds the force expenditure required to clamp off the organic tissue, and the tissue clamp can then be pushed out of application crosspiece 7.

However, it is also possible to do without shearing off of guide pins 9, 14, if longitudinal grooves 17, 21, and 22 are continued beyond distal holder 5 all the way to the end of the application crosspiece, and guide pins 9, 14 can exit from the latter. In this case, fixation of distal clamping bar 1 takes place by fixation shoulder 10, with the corresponding crosswise groove 11.

Accordingly, while only a few embodiments of the present invention have been shown and described, it is obvious that many changes and modifications may be made thereunto without departing from the spirit and scope of the invention.

What is claimed is:

1. A device for clamping off organic tissue, comprising: a tissue clamp that can be released from a distal end of an application instrument, said clamp having proximal and distal clamping bars made of absorbable material;
   an application crosspiece having an internal pushing device and a guide groove for receiving the distal and proximal clamping bars, the proximal clamping bar being displaceable in the guide groove by said internal pushing device, while the distal clamping bar maintains its position until the organic tissue has been clamped off, the application crosspiece having holders for accommodating the clamping bars;
   wherein the proximal clamping bar has at least one guide pin on each side of its base, and the distal clamping bar has at least one guide pin on each side of its base or has a fixation shoulder, and wherein the guide pins on the proximal clamping bar and the guide pins or shoulder on the distal clamping bar are configured to fit into crosswise grooves in the application crosspiece, so that the clamping bars are inserted into said crosswise grooves perpendicular to an axis of the application crosspiece; wherein the proximal clamping bar is displaced in the guide groove of the application crosspiece and in longitudinal grooves formed on both sides of the crosspiece on an inside of the crosspiece, with the guide pins; wherein the proximal clamping bar has a holder pin on its base, disposed in a direction of the distal end, which holder pin engages into a corresponding holder bore of the distal clamping bar when the proximal clamping bar is displaced by the internal pushing device, and produces a force-fit and shape-fit connection with this holder bore, while simultaneously clamping off the organic tissue; and wherein if the distal and proximal clamping bars have guide pins, the guide pins are constructed so that they shear off if an expenditure of force required to clamp off the organic tissue is exceeded, and wherein if the distal clamping bar has a fixation shoulder, the fixation shoulder has such an elasticity that the clamping bars, with the organic tissue clamped off between them, as a tissue clamp, can be released from the application crosspiece by means of the pushing device, in a direction of the distal end.

2. The device according to claim 1, wherein the proximal clamping bar has two guide pins, disposed in pairs in the a longitudinal direction, on each side of the proximal clamping bar, and the application crosspiece has two crosswise grooves on each side, into which the guide pins engage when the proximal clamping bar is inserted into the application crosspiece.

3. The device according to claim 1, wherein a face surface of the pushing device and an opposite face surface of the base of the proximal clamping bar have corresponding profilings.

4. The device according to claim 1, wherein the holder pin and corresponding the holder bore are configured to be slightly conical, cylindrical, cone-shaped or pyramid-shaped.

5. The device according to claim 1, wherein the holder pin and the holder bore have a corresponding cross-section such that the clamping bars remain parallel while the organic tissue is clamped off, and so that secure reciprocal fixation of the clamping bars in the tissue clamp as an end position is ensured.

6. The device according to claim 1, wherein the clamping bars are disposed biased to one another, so that the clamping bars are disposed at a greater distance to one another at a location close to the application crosspiece than at their ends.

7. The device according to claim 1, wherein multiple longitudinal grooves are provided, and the cross-section of the guide groove is configured in T shape or double T shape, in which longitudinal grooves the guide pins on the base of the proximal clamping bar can be displaced.

8. The device according to claim 1, wherein the distal clamping bar has a fixation shoulder that extends lengthwise in the crosswise groove, and is elastically configured so that when the force expenditure required for clamping off the organic tissue is exceeded, said shoulder deforms so that the tissue clamp is displaced out of the application crosspiece by means of the pushing device and comes off.

9. The device according to claim 1, wherein said application crosspiece comprises a one-piece application crosspiece.

* * * * *